United States Patent

Ziegler

(10) Patent No.: US 7,130,027 B2
(45) Date of Patent: Oct. 31, 2006

(54) REFLECTION-PHOTOMETRIC ANALYTICAL SYSTEM

(75) Inventor: Friedrich Ziegler, Stuttgart (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 10/620,217

(22) Filed: Jul. 15, 2003

(65) Prior Publication Data

US 2004/0012790 A1  Jan. 22, 2004

(30) Foreign Application Priority Data

Jul. 19, 2002 (DE) ............................... 102 33 087

(51) Int. Cl.
*G01C 3/00* (2006.01)
*G01N 33/48* (2006.01)
*G01N 21/17* (2006.01)
*G02B 27/40* (2006.01)

(52) U.S. Cl. .................. 356/3.01; 356/36; 356/39; 422/82.05; 250/201.6

(58) Field of Classification Search ....... 356/3.01–309, 356/602, 612, 36, 39, 631, 904, 928; 250/559.31, 250/201.3, 201.4, 201.6; 422/82.05
See application file for complete search history.

(56) References Cited

U.S. PATENT DOCUMENTS

| | | | | |
|---|---|---|---|---|
| 4,477,185 A * | 10/1984 | Berger et al. | ............ | 356/152.2 |
| 4,577,095 A * | 3/1986 | Watanabe | ................ | 250/201.2 |
| 4,958,920 A * | 9/1990 | Jorgens et al. | ............... | 359/392 |
| 5,136,149 A * | 8/1992 | Fujiwara et al. | .......... | 250/201.5 |
| 5,270,527 A * | 12/1993 | Salzmann | ................. | 250/201.3 |
| 5,546,189 A | 8/1996 | Svetkoff et al. | ............ | 356/376 |
| 5,587,794 A * | 12/1996 | Mizutani et al. | ............ | 356/623 |
| 5,604,344 A * | 2/1997 | Finarov | .................... | 250/201.3 |
| 5,654,799 A | 8/1997 | Chase et al. | ................ | 356/371 |
| 5,801,817 A | 9/1998 | Riedel | ........................ | 356/4.07 |
| 5,841,149 A * | 11/1998 | Spink et al. | ........... | 250/559.29 |
| 6,028,671 A * | 2/2000 | Svetkoff et al. | ............ | 356/368 |
| 6,542,248 B1 * | 4/2003 | Schwarz | ..................... | 356/600 |
| 6,555,836 B1 * | 4/2003 | Takahashi et al. | ..... | 250/559.19 |
| 6,624,403 B1 * | 9/2003 | Chen et al. | ............. | 250/201.2 |
| 2002/0078580 A1* | 6/2002 | Haugen et al. | ................ | 33/533 |

FOREIGN PATENT DOCUMENTS

| | | |
|---|---|---|
| EP | 0 917 852 A2 | 5/1999 |
| EP | 1 241 464 A1 | 9/2002 |
| EP | 1 382 959 A1 | 1/2004 |
| JP | 05010948 A | 1/1993 |

* cited by examiner

*Primary Examiner*—Thomas H. Tarcza
*Assistant Examiner*—Isam Alsomiri
(74) *Attorney, Agent, or Firm*—Marilyn L. Amick; Roche Diagnostics Operations, Inc.

(57) ABSTRACT

This invention generally relates to a reflection-photometric analytical system having a measuring head comprising a source of radiation and a radiation detector for the reflection-photometric analysis of a target surface of a test object arranged at a distance from the measuring head and in particular of a test strip for body fluids such as urine or blood. A triangulation unit operating on the basis of optical triangulation is proposed for contact free checking of the distance in order to monitor or regulate the measuring distance.

22 Claims, 3 Drawing Sheets

REFLECTION-PHOTOMETRIC ANALYTICAL SYSTEM

PRIORITY CLAIM

This application claims priority under 35 U.S.C § 119 to Application No: 102 33 087.5 filed in Germany on Jul. 19, 2002.

BACKGROUND OF THE INVENTION

The invention concerns a reflection-photometric analytical system having a measuring head comprising a source of radiation and a radiation detector for the reflectometric analysis of a target surface of a test object arranged at a distance from the measuring head and in particular of a test strip for body fluids such as urine or blood. The invention also concerns a corresponding measuring method.

Systems of this type are used particularly in the field of clinical analysis in order to determine the presence and concentration of certain analytes in a sample liquid by means of test strips. A spectroscopic analysis of radiation reflected from irradiated test fields of the test strips is carried out in automated instruments. A critical factor for reflectometric measurement is a constant measuring distance where it is necessary to take into account that the test fields can have different heights and that absorption of the sample liquid can result in different degrees of swelling. It has been attempted to reduce the distance dependency by using a receiving optical system having a long focal length and a greatly reduced optical aperture which is aligned perpendicularly to the target surface. However, this requires a large space and the signal currents of the photodetector are small and thus require complicated measurement instrumentation to process them.

A sensor for distance measurement and a control unit for adjusting the measuring distance has already been proposed in JP-A 03-166738 (publication number 10948/1993) in a similar context. However, it does not disclose anything about the operating principle of the distance detection. A general problem is that the surface properties of test strips can vary greatly due to the application of sample liquid since almost dry, rough surfaces as well as wet and hence shiny surface may be present.

This was the starting point for the invention whose object is to avoid the disadvantages of the prior art and to improve an analytical system and a method of the type described above in such a manner that a high measuring accuracy is achieved even when the target surface has a variable height profile. In particular it should enable a reliable control of the measuring distance.

The combination of features stated in the claims are proposed to solve this problem. Advantageous embodiments and further developments of the invention are derived from the dependent claims.

SUMMARY OF THE INVENTION

The invention is based on the idea that a change in the measuring distance can be detected in a position resolving manner by a corresponding change in the path of the rays. Correspondingly the invention proposes a triangulation unit operating on the basis of optical triangulation for checking the distance between the measuring head and target surface without contact. The influence of variations in the height of the target surface can be eliminated in a simple manner by this means without impairing the efficiency of the photometric measuring system. This would enable any measuring sites to be probed on the target surface and in particular also measuring sites that reflect completely diffusely. The triangulation method has a high distance resolution and can operate substantially in real time during positioning movements.

The triangulation unit advantageously has a light emitter directed onto the target surface in an axis of incidence and a light receiver pointing towards the target surface oriented in a receiving axis. In this connection it is advantageous for reference measurements when the incidence and receiving axis intersect a reference point at a predetermined angle where the reference point defines a set position of the target surface.

In order to preferably detect diffusely back-scattered light, it is advantageous when the incidence and receiving axis enclose different angles relative to a perpendicular on the target surface.

In order to detect the light deflection correlating with the change in distance, a preferred embodiment provides that the light receiver has a position-resolving sensor at right angles to the receiving axis. In this case a PSD sensor (position sensing detector), CCD sensor (charge coupled device) or multi-element diode sensor can be advantageously used.

In a particularly simple embodiment the light receiver is a double sensor with two single sensors in particular single diodes arranged side by side and preferably symmetrically to the receiving axis. This allows the detection of distance variations by means of the resulting differences in the illumination of the single sensors.

Another advantageous embodiment provides that the light receiver has a collecting optical system whose optical axis defines the receiving axis for focussing the light reflected from the target surface, and that the light emitter has a light source, in particular a point light source and a collimating optical system whose optical axis defines the incidence axis for producing a light beam incident on the target surface.

According to a further preferred embodiment of the invention the light emitter has a modulation stage for the time-varying and preferably pulsed shaped actuation of a light source. This improves the tolerance compensation of the reflection factor and simplifies the detection electronics. For this it is preferable that the light emitter has an edge generator to produce non-linear and preferably exponentially increasing or decreasing light pulses.

The triangulation unit advantageously has a signal processing circuit for determining changes in the distance relative to a reference position on the target surface. In order to relate changes in position to a time measurement it is advantageous when the signal processing circuit has a comparator and a timer to determine the time interval of specified signal amplitudes of output signals of the triangulation unit.

Another preferred embodiment provides a control device that interacts with the triangulation unit to set a specified distance between the target surface and measuring head by means of a servodrive.

An additional benefit can be achieved when the path of the measuring head can be recorded by a path measuring device to determine a height profile of the test object and that the path measuring device has a height profile store to identify the test object.

Instead of the distance regulation it is also conceivable that the triangulation unit has an evaluation unit to standardize the results of the photometric analysis on the basis of the distance between the target surface and measuring head.

An additional functional simplification is achieved when the light source is at the same time the light emitter and/or the radiation detector is at the same time the light receiver of the triangulation unit.

The above-mentioned object is achieved by a method in which the measuring distance between the measuring head and target surface is examined without contact by a triangulation unit on the basis of optical triangulation. Changes in the distance are preferably detected relative to a specified distance of the target surface by means of an appropriate light deflection onto a light receiver of the triangulation unit. Another advantageous procedure provides that the measuring distance is kept constant by means of a control device.

BRIEF DESCRIPTION OF THE DRAWINGS

The invention is elucidated further in the following on the basis of an embodiment which is shown schematically in the drawing.

DETAILED DESCRIPTION OF THE INVENTION

Figure 1:
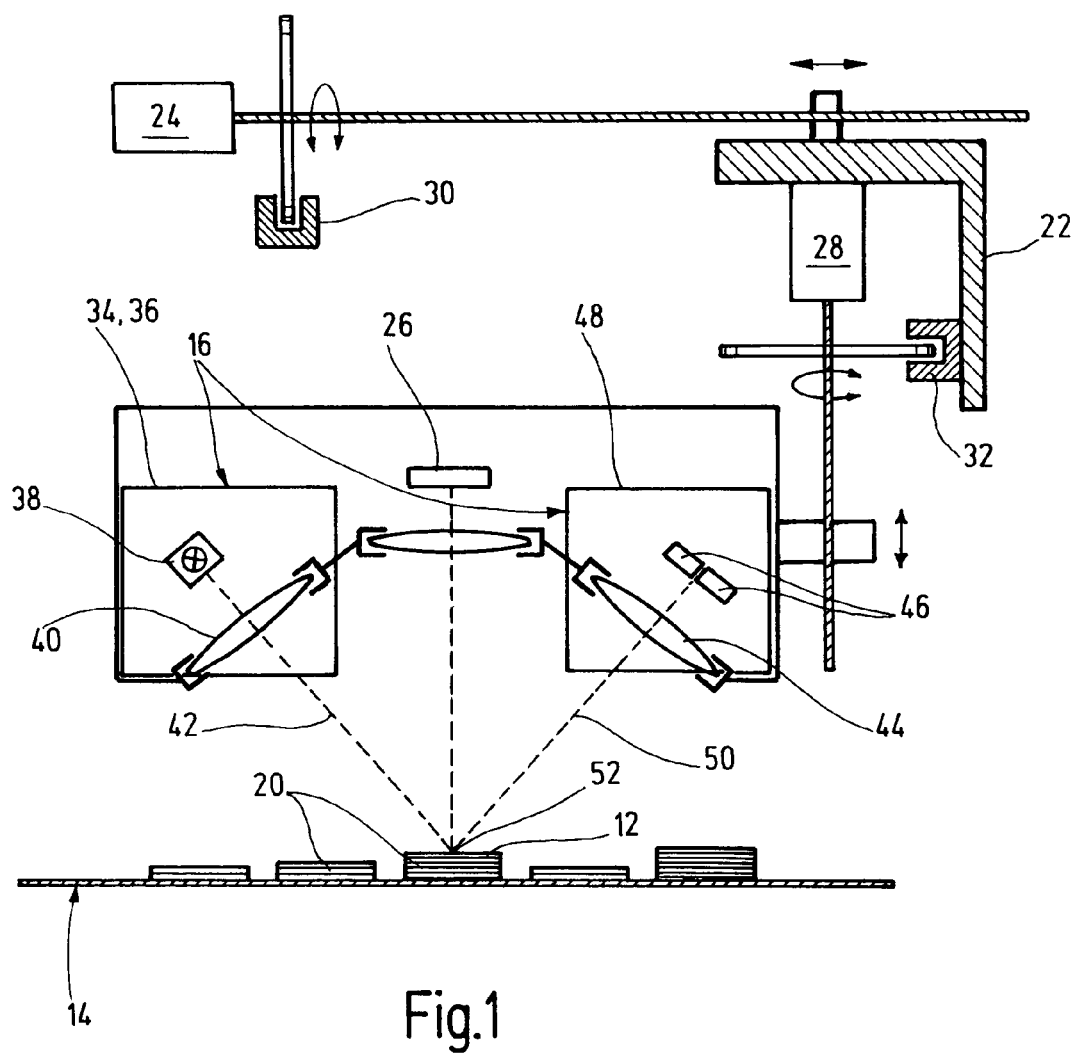
FIG. 1 shows a diagram of a reflection photometer having a triangulation unit to control the measuring distance.

The reflection photometric analytical system shown in the diagram essentially consists of a measuring head 10 for the reflectometric examination of the target surface 12 of an analytical test strip 14, a triangulation unit 16 to check or detect the measuring distance between the measuring head 10 and target surface 12 and a control device 18 to set a constant measuring distance.

As shown in FIG. 1, the test strip 14 has different test fields 20 which are used to detect specific analytes in a body fluid to be examined such as urine or blood. For this purpose the measuring head 10 can be moved on a slide 22 towards the strip by means of a forward feed drive 24 during which the photodetector 26 of the photometer detects the light reflected from the target surface 12 of the test fields 20. In this process a constant measuring distance can be set between the photodetector 26 and the target surface 12 of the test fields 20 of different thicknesses by means of a adjusting drive 28 of the control device 18. Angle transmitters 30, 32 that are sensitive to the direction of rotation are located on the rotating spindles of the drives 24, 28 to detect the path of travel of the measuring head 10. These generate counting pulses during a rotary movement from which a linear path can be calculated according to the spindle pitch.

The triangulation unit 16 has a light emitter 34 which is at the same time the radiation source 36 for the reflectometric measurement. The light emitter 34 comprises a semiconductor diode 38 as a light source and a collimatic optical system 40 to produce a light beam in the direction of an incidence axis 42 directed onto the target surface 12.

In order to detect the light beam reflected from the target surface 12, the triangulation unit 16 has a light receiver 48 comprising a collecting optical device 44 and a double diode sensor consisting of two single diodes 46. The optical axis of the collecting optical device 44 defines a receiving axis 50 which intersects the incidence axis 42 at a reference point 52 that determines a set position on the target surface 12. The single diodes 46 are arranged side by side and symmetrically to the receiving axis 50 and their receiving surface faces the target surface 12 such that both single diodes 46 are illuminated equally in the set position. When a movement occurs away from the set position, the focus of the received light beam moves correspondingly transversely to the receiving axis 50 in the plane defined by the incidence and receiving axis and as a result one of the single diodes 46 is illuminated more strongly than the other. The difference in illumination corresponds to the change in distance.

Figure 2:
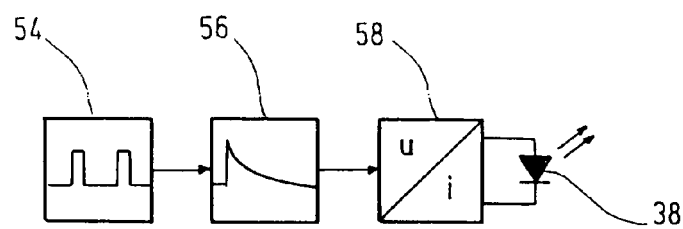
FIG. 2 shows a block diagram of a generator circuit for triggering the pulses of a light emitter of the triangulation unit.

As illustrated in FIG. 2 the light source 38 can be actuated in pulses by means of a generator circuit. This consists of a modulation stage 54 to determine the pulse intervals, an edge generator 56 to produce exponentionally decreasing light pulse flanks and a voltage current converter 58 to supply the light source 38 with power whereby the light intensity follows the time course of the current pulses.

Figure 3:
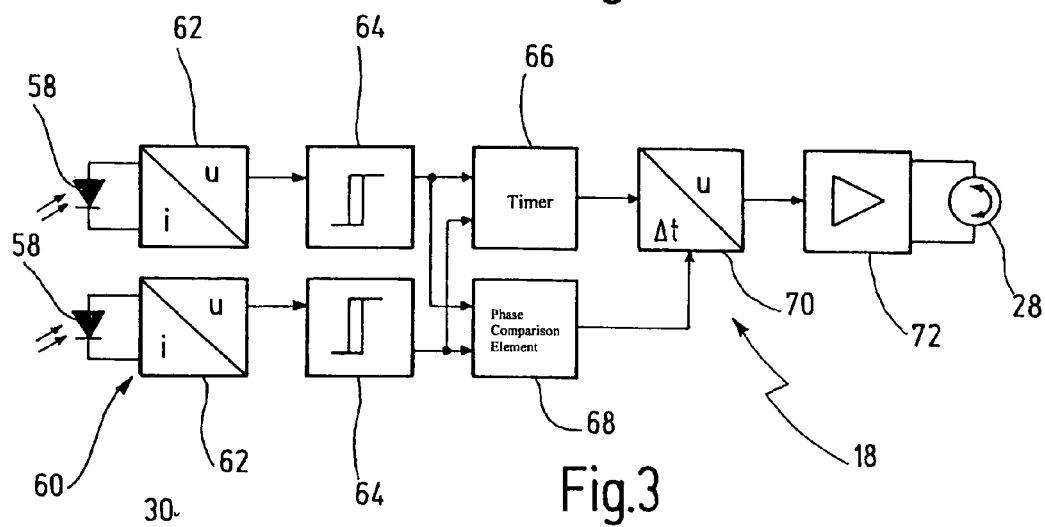
FIG. 3 shows a block diagram of a distance control device interacting with the triangulation unit.

As shown in FIG. 3 the output signals of the light receiver 34 can be analysed by a downstream signal processing circuit 60 in the sense of a distance check which is described below in more detail. For this purpose the single diodes 46 are each connected via a current-voltage converter 62 and a threshold value comparator 64 with a timer 66 and a phase comparison element 68. A subsequent integrator stage 70 converts the time difference of the comparator signal allocated to a light pulse into a corresponding voltage signal with the correct polarity sign. This can be fed as an adjusting signal to an analogue amplifier stage 72 to actuate the positioning drive 28. In this manner the circuit shown in FIG. 3 forms the control device 18 which ensures the maintenance of the reference position and a predetermined measuring distance when measuring the various test fields 20.

Figure 4:
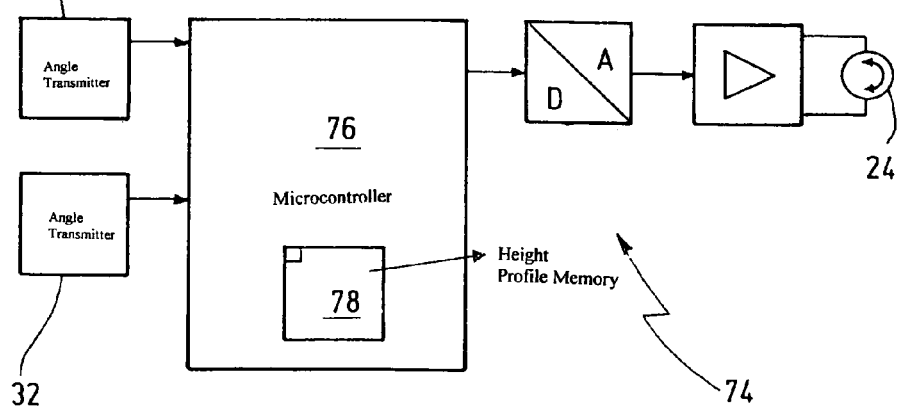
FIG. 4 shows a block diagram of a path recording system to determine the height profile of the test object to be examined and FIG. 5 shows a time diagram of light signals detected by the triangulation unit.

The path recording system 74 shown in FIG. 4 enables an identification of the test strip 14 on the basis of the height profile of its test fields 20. For this purpose the counting pulses of the angle transmitter 30, 32 are counted in a microcontroller 76 in order to determine the current position or path of travel of the measuring head 10 starting from an initial position. The distance control results in a height profile when the forward feed drive 24 is operated which can be compared with stored data in a height profile memory 78 in order to decide on the validity of the measurement.

In general measuring distance by triangulation is based on a comparison of similar triangles which are subtended between the collecting lens and receiver as an object triangle between the object and collecting lens and as an image triangle between the collecting lens and receiver in accordance with the optical path. According to the invention the method is limited to measurements relative to a reference plane in which an image point of the detection light (diffusely) reflected by the test object is deflected on the receiver surface by a change in the distance. The spatial deflection can be converted back into a time measurement due to the pulse modulation of the detection light as a result of which tolerances in the optical efficiency of the measuring system due to the exponential intensity time course have essentially no effect.

Figure 5:
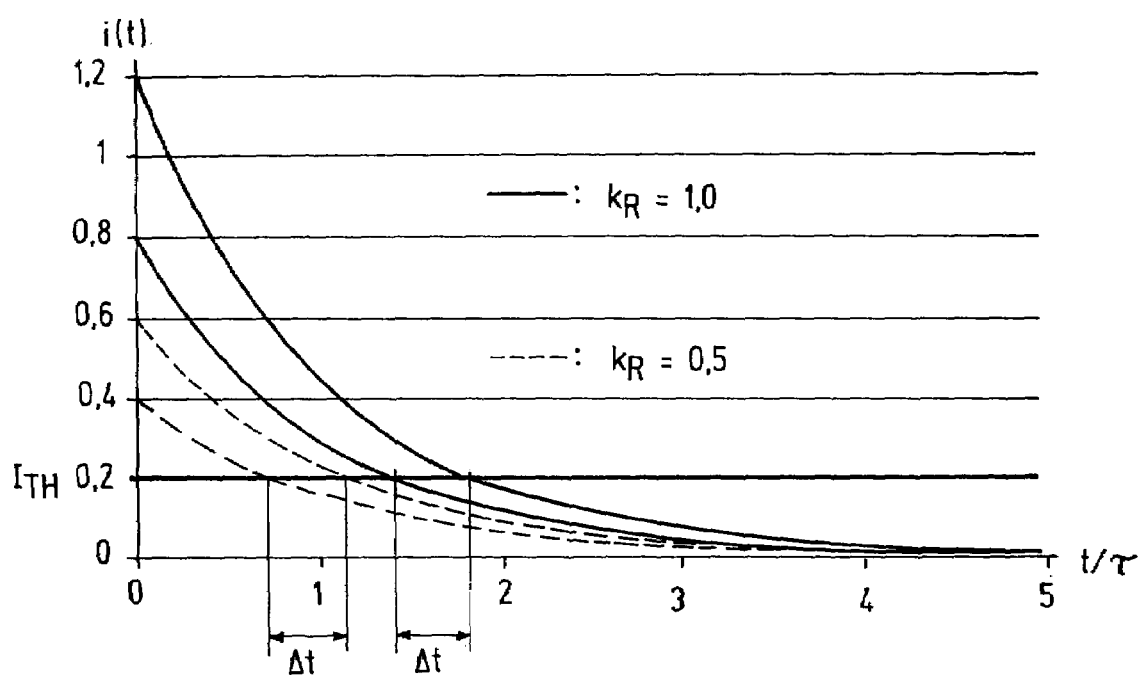

This mode of operation is further illustrated in FIG. 5 by a time course of the receiver signals of the single diodes 46 for the case of a first reflection factor of the target surface 12 (continuous curves) and a second reflection factor which is reduced by half (dashed curves). It is assumed that there is a deviation from the reference position which results in an unsymmetric illumination of the single diodes 46 and correspondingly to different initial amplitudes. In the case of a decreasing e-function-modulated illumination intensity, this results in different trigger times for the threshold value $I_{Th}$ of the comparators 64 whose time difference Δt is detected by means of the timer 66. The direction of the change in distance is determined by the time sequence of the trigger signals in the phase comparison element 68. As shown in FIG. 5 the time intervals Δt are equal for both reflection factors. In mathematical terms it can be shown that in the neighbourhood of the reference distance the time different Δt is independent of the reflection factor and essentially linearly dependent on the change in the distance Δh. Hence the arrangement described above creates a robust control unit with good control properties.

The invention claimed is:

1. An analytical system for reflectometric analysis of an analyte in a sample liquid comprising:
    a test strip provided with a test field for application of the sample liquid wherein the test field including the applied sample liquid has a target surface;
    a measuring head arranged at a distance from the target surface, wherein the measuring head comprises a source for radiating the target surface and a detector for measuring radiation reflected by the target surface;
    an optical triangulation unit for detecting the distance between the measuring head and the target surface, wherein the triangulation unit comprises a light emitter directed towards the target surface in an incidence axis and a light receiver pointing towards the target surface in the direction of a receiving axis and wherein the incidence and receiving axis intercept at a reference point; and
    a control device for adjusting the distance between the measuring head and the target surface to a predetermined value, thereby permitting accurate analysis of the analyte by the measuring head.

2. The analytical system as claimed in claim 1, wherein the reference point defines a reference position of the target surface.

3. The analytical system as claimed in claim 1, wherein the incidence and receiving axis enclose different angles relative to a perpendicular on the target surface.

4. The analytical system as claimed in claim 1, wherein the light receiver has a sensor, which is position-resolving at right angles to the receiving axis.

5. The analytical system as claimed in claim 4, wherein the sensor is a PSD sensor, CCD sensor or multi-element diode sensor.

6. The analytical system as claimed in claim 1, wherein the light receiver is a double sensor with two single sensors preferably arranged next to one another and symmetrically to the receiving axis.

7. The analytical system as claimed in claim 1, wherein the light receiver has a collecting optical system whose optical axis defines the receiving axis for focussing the light reflected from the target surface.

8. The analytical system as claimed in claim 1, wherein the light emitter has a light source and a collimating optical system whose optical axis defines the incidence axis for generating a light beam which is incident on the target surface.

9. The analytical system as claimed in claim 1, wherein the light emitter has a modulation stage for the time-varying actuation of a light source.

10. The analytical system as claimed in claim 1, wherein the light emitter has an edge generator to produce non-linear increasing or decreasing light pulses.

11. The analytical system as claimed in claim 1, wherein the triangulation unit has a signal processing circuit for determining changes in the distance relative to a reference position on the target surface.

12. The method as claimed in claim 11, wherein the changes in the distance relative to a reference distance of the target surface are detected by means of a corresponding light deflection onto a light receiver of the triangulation unit.

13. The method as claimed in claim 11, wherein the distance is kept constant at the predetermined value by means of a control device.

14. The analytical system as claimed in claim 11, wherein the signal processing circuit has a comparator and a timer to determine the time interval between specified signal amplitudes of output signals of the triangulation unit.

15. The analytical system as claimed in claim 1, wherein the control device sets the constant measuring distance between the target surface and measuring head by means of a servodrive.

16. The analytical system as claimed in claim 1, further comprising a path measuring device to record the path of the measuring head for determining a height profile of the test object.

17. The analytical system as claimed in claim 16, wherein the path measuring device has a height profile store to identify the test object.

18. The analytical system as claimed in claim 1, further comprising an evaluation unit to standardize the results of the photometric triangulation unit on the basis of the distance between the target surface and the head.

19. The analytical system as claimed in claim 1, wherein the light source is at the same time the light emitter or the radiation detector is at the same time the light receiver of the triangulation unit.

20. The analytical system as claimed in claim 1, wherein the light emitter has a modulation stage for the pulse-shaped actuation of a light source.

21. The analytical system as claimed in claim 1, wherein the light emitter has an edge generator to produce exponentially increasing or decreasing light pulses.

22. A method for reflectometric analysis of an analyte in a sample liquid comprising:
    applying the sample liquid to a surface of a test strip to form a test field having a target surface;
    arranging the target surface as a distance from a measuring head, wherein the measuring head comprises a source for radiating the sample and a detector for measuring radiation reflected by the sample;
    detecting the distance between the measuring head and target surface by means of an optical triangulation unit comprising a light emitter directed towards the target surface in an incidence axis and a light receiver pointing towards the target surface in the direction of a receiving axis; and
    adjusting, by means of a control device, the distance between the measuring head and the target surface to a predetermined value, thereby permitting accurate analysis of the analyte by the measuring head.

* * * * *